(12) United States Patent
Fallon

(10) Patent No.: US 6,534,063 B1
(45) Date of Patent: Mar. 18, 2003

(54) METHODS FOR TREATING PERVASIVE DEVELOPMENT DISORDERS

(76) Inventor: Joan M. Fallon, 830 Pelhandale Ave., New Rochelle, NY (US) 10801

( * ) Notice: Subject to any disclaimer, the term of this patent is extended or adjusted under 35 U.S.C. 154(b) by 0 days.

(21) Appl. No.: 09/466,559

(22) Filed: Dec. 17, 1999

(51) Int. Cl.[7] ................................................ A61K 38/16
(52) U.S. Cl. ............................. 424/198.1; 435/4; 514/2
(58) Field of Search .................................. 600/350, 343; 435/4; 424/198.1; 514/2

(56) References Cited

U.S. PATENT DOCUMENTS

| | | |
|---|---|---|
| 4,079,125 A | 3/1978 | Sipos |
| 5,250,418 A | 10/1993 | Moller et al. |
| 5,686,311 A | 11/1997 | Shaw |
| 5,750,104 A | 5/1998 | Sipos |
| 5,985,891 A | 11/1999 | Rowe |
| 6,020,310 A | 2/2000 | Beck et al. |
| 6,020,314 A | 2/2000 | McMichael |

FOREIGN PATENT DOCUMENTS

| | | |
|---|---|---|
| DE | 4332985 | 3/1995 |
| WO | WO 9852593 | 11/1998 |
| WO | WO9964059 | 12/1999 |
| WO | WO 0009142 | 2/2000 |

OTHER PUBLICATIONS

Horvath et al. Improved social and language skills after secretin administration in patients with autistic spectrum disorders (Jan. 1998) J. of the Association of Academic Minority Physicians. 9 (1): 9–15.*

Marlicz and Chrzanowska Determination of chymotrypsin in the stool in the diagnosis of chronic pancreatitis (1988) WIAD LEK 41(11): 704–707 (abstract only).*

Remtulla et al., "Stool Chymotrypsin Activity Measured by a Spectrophotometric Procedure to Identify Pancreatic Disease in Infants", Clinical Biochemistry, vol. 19, pp. 341–342, Dec. 1986.

Kaspar et al., "New Photometric Assay for Chymotrypsin in Stool", Clinical Chemistry, vol. 30, No. 11, pp 1753–57, (1984).

Horvath, et al., "Improved Social and Language Skills After Secretin Administration in Patients with Autistic Spectrum Disorders", Journal of the Association for Academic Minority Physicians, vol. 9, No. 1, pp. 9–15, Jan., 1998.

* cited by examiner

Primary Examiner—Lorraine Spector
Assistant Examiner—Dong Jiang

(57) ABSTRACT

A method of utilizing the fecal chymotrypsin level of an individual as a measure of the success of secretin, other neuropeptides, and peptides or digestive enzyme administration to such individuals, and in particular, as a prognosticative of potential secretin, other neuropeptides, peptides, and digestive enzyme administration for persons having ADD, ADHD, Autism and other PDD related disorders.

8 Claims, 17 Drawing Sheets

METHODS FOR TREATING PERVASIVE DEVELOPMENT DISORDERS

BACKGROUND

1. Technical Field

The present invention relates generally to a method for treating individuals diagnosed with a form of PDD (pervasive development disorder) and other disorders such as ADD (attention deficit disorder) and ADHD (attention deficit hyperactivity disorder). More specifically, the present invention is directed to therapeutic method for treating individuals with such disorders by administering secretin, other neuropeptides, peptides, and/or digestive enzymes, as well as a prognosticative method for determining the potential effectiveness of the administration of secretin, other neuropeptides, peptides, and/or digestive enzymes for the treatment of such disorders.

2. Description of Related Art

PDDs are a class of disorders defined by both American and International diagnostic systems (i.e., the Diagnostic and Statistical Manual of Mental Disorders, 4th edition (DSM-IV) and World Health Organization: International Classification of Diseases, Tenth revision (ICD-10)). The spectrum of PDDs include disorders such as Autism, Aspergers, ADD, and ADHD. PDDs are typically characterized by multiple distortions in the development of basic psychological functions that are involved in the development of social skills and language, such as attention, perception reality testing and motor movement. In addition, many children diagnosed with Autism, for example, suffer from primary diffuse gastrointestinal problems such as protracted diarrhea and constipation. Although PDDs are currently of unknown etiology, many conventional methods, such as dietary alteration, behavioral modification, and medication, have been utilized for treating individuals suffering from PDD related disorders. Unfortunately, PDD related disorders have no known treatment beyond that which is symptomatic, and these conventional methods have proven unsuccessful in allowing such children and adults to become symptom, or disorder free.

A child which displays signs of developmentally inappropriate inattention, impulsivity and hyperactivity is typically diagnosed as having ADD and/or ADHD. With these disorders, there can be marked disturbances of organization, distractibility, impulsivity, restlessness, and other disturbances of language and/or social behavior. A combination of psychiatric care and medicine is typically used for treating children with ADD and ADHD.

It was recently discovered that the administration of secretin, a gastrointestinal peptide hormone, to children diagnosed with Autism resulted in ameliorating the symptoms associated with Autism. This finding was published in the article by Horvath et al., entitled *Improved Social and Language Skills After Secretin Administration In Patients with Autistic Spectrum Disorders*, Journal of the Association for Academic Minority Physician Vol.9 No. 1, pp. 9–15 , January, 1998. The secretin administration, as described in Horvath, was performed as a diagnostic procedure, i.e., to stimulate pancreaticaobiliary secretion during an upper gastrointestinal endoscopy, rather than as a therapeutic procedure. Although the specific mechanism by which the secretin improved the autistic-related symptoms was not specifically identified, Horvath postulated that secretin may have had a direct or indirect effect on the central nervous system. What is important, however, is that this was the first time that gastrointestinal problems of autistic children were linked to a possible etiology in Autism.

Accordingly, in view of such findings, a method for determining whether an individual suffering from a disorder in the PDD spectrum will benefit from the administration of secretin, other neuropeptides, peptides and/or digestive enzymes, as well as a therapeutic method for treating such individuals with the administration of secretin, other neuropeptides, peptides and/or digestive enzymes, are highly desired.

SUMMARY OF THE INVENTION

The present invention is directed to a method of analyzing the chymotrypsin level of an individual to determined the potential benefit of the administration of secretin, other neuropeptides, and peptides or digestive enzyme administration to such individual, and in particular, as a prognosticative of potential secretin, other neuropeptides, peptides, and digestive enzyme administration for individuals diagnosed as having ADD, ADHD, Autism and other PDD related disorders.

In one aspect, a method for determining the efficacy of secretin, other neuropeptides, peptides, or digestive enzymes for the treatment of an individual diagnosed with a pervasive developmental disorder (PDD) comprises obtaining a sample of feces from an individual, determining a quantitative level of chymotrypsin present in the sample, and correlating the quantitative level of chymotrypsin determined to be present in the sample with the PDD to determine the efficacy of treating the individual with secretin, other neuropeptides, peptides, or digestive enzyme administration.

In another aspect, a therapeutic method for treating an individual diagnosed with a PDD pervasive developmental disorder comprises determining the efficacy of the administration of secretin, other neuropeptides, peptides, and digestive enzyme for the treatment of the individual based on a measure of the individual's chymotrypsin level, and administering secretin, other neuropeptides, peptides, or digestive enzymes to the individual based on the determination of the measure of the individual's chymotrypsin level.

The present invention involves determining the presence of abnormal protein digestion of individuals, especially children, by measuring the chymotrypsin levels so as to determine if the individual is likely to benefit from the administration of secretin, digestive enzymes, peptides and/or neuropeptides. Although there have been methods to test fecal samples for indications of cystic fibrosis and pancreatic diseases in infants, none of the known methods have tested fecal samples in determining the benefits of administering secretin, other neuropeptides, peptides and/or digestive enzymes to individuals suffering from a PDD. Indeed, in so far as an individual's fecal chymotrypsin level is a broad measure of protein and fat digestion, such levels can be applied to all those who may benefit from improvements in this mode of digestion. Furthermore, as low measures of fecal chymotrypsin expresses an abnormality of protein digestion, it is postulated that an improvement of protein digestion to promote normal growth and development of an individual suffering from a PDD by the administration of secretin, other neuropeptides, peptides and/or digestive enzymes, can ameliorate the symptomatologies of PDDs.

Accordingly, in another aspect of the present invention, a therapeutic method is provided for treating an individual diagnosed with a PDD including but not limited to Autism, Aspergers, ADD and ADHD, comprising the steps of:

determining the effectiveness of secretin administration for the treatment of the individual based on a measure of the individual's chymotrypsin level; and administering secretin therapy to the individual based on the determination of the measure of the individuals chymotrypsin level.

In yet another aspect, the therapeutic method involves administering a fecal chymotrypsin test to measure an individual's fecal chymotrypsin level. Preferably, an enzymatic spectrophotometry method is used for measuring the fecal chymotrypsin level of the individual. Upon determinating that an individual has an abnormal level of chymotrypsin, the individual is preferably administered 1 U/kg of body weight of porcine or human secretin by means of an intravenous push method. This method can be described as the administration of an IV push of saline solution and secretin to equal 1 U/kg of body weight. The individual then receives 1 unit test dose (absolute). A period of one minute is allowed to pass to determine if the individual has any allergic reactions to the secretin. After one minute has elapsed, if no urticarial reaction or any other allergic reaction has occurred, the remainder of the dose is administered. Subsequent fecal chymotrypsin samples are then gathered at one week intervals post administration to determine any changes in the chymotrypsin levels.

These and other aspects, features and advantages of the present invention will be described and become apparent from the following detailed description of preferred embodiments, which is to be read in connection with the accompanying drawings.

DETAILED DESCRIPTION OF PREFERRED EMBODIMENTS

Figure 1:
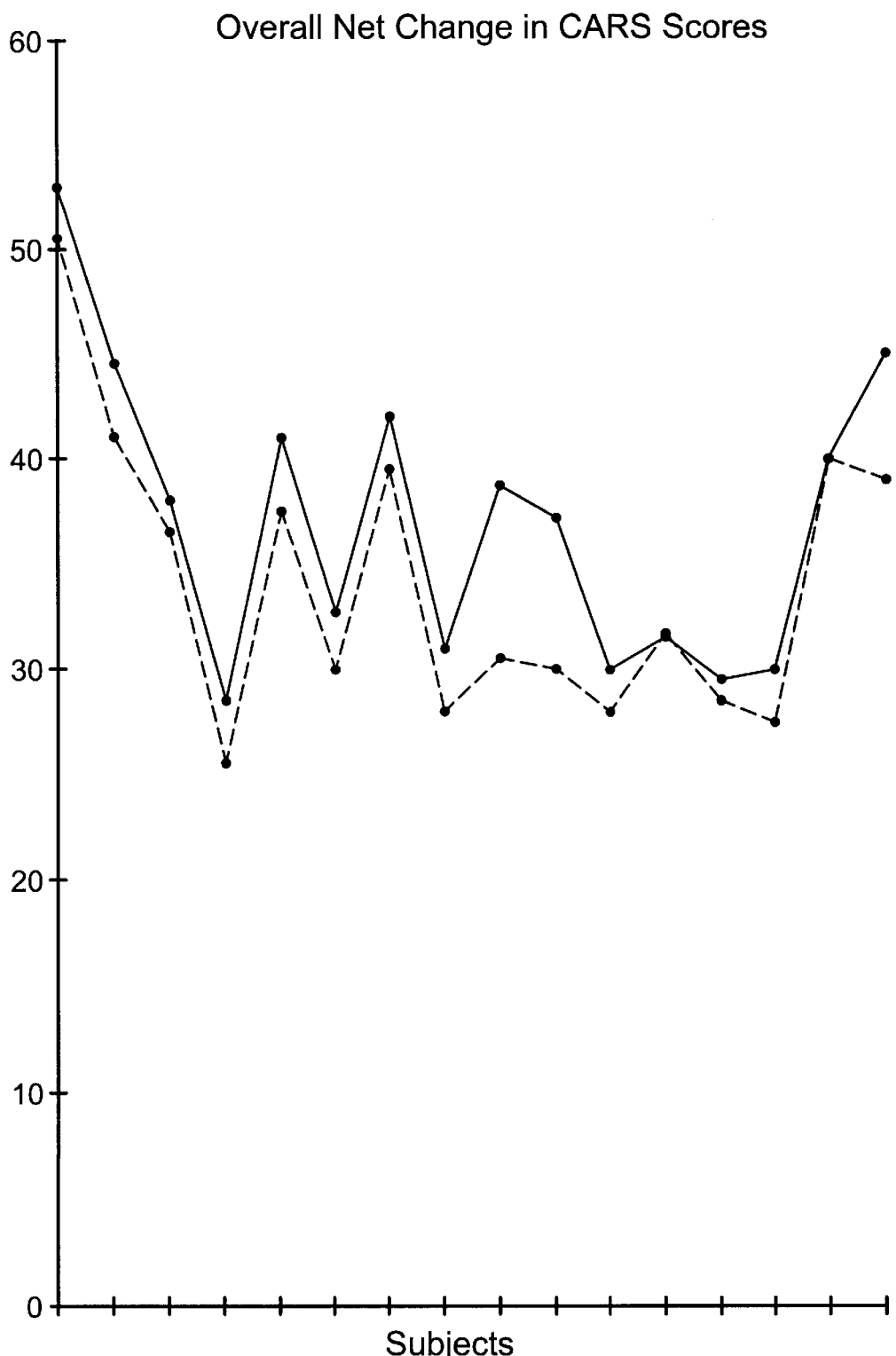
FIG. 1 illustrates the overall net change in results of a CARS test (Childhood Autism Rating Scale) depicting behavior of 16 autistic children pre-secretin and post-secretin administration, where the solid lines indicate pre-secretin scores and the dotted lines indicate post-secretin scores.

The present invention is directed to a method of analyzing chymotrypsin levels in persons, especially children, as a measure of the success of administering secretin, other neuropeptides, peptides and/or digestive enzymes for the therapeutic treatment of ADD, ADHD, Autism, Aspergers and other PDD related disorders. The use of secretin for the treatment of Autism is presently in the investigational stages. When the positive affects of the neuropeptide secretin on childhood autism were first discovered and published, research was conducted by the present inventor to formulate a process that would enable one to definitively determine if individuals, especially children, having a PDD could be tested prior to the administration of secretin for its possible efficacy for treating PDD. Tests were performed to measure the fecal chymotrypsin levels (referred to herein as Fecal Chymotrypsin Test) in children who span the entire PDD spectrum and whose symptomotology place them in this DSM IV category. As demonstrated below, such tests revealed that a majority of the children diagnosed with autism, ADD and ADHD, for example, had abnormal chymotrypsin levels. It is believed that such abnormal levels of chymotrypsin have not heretofore been identified in the PDD population of children and adults.

It is postulated that the abnormal levels of chymotrypsin are due to the inability of the pancreas to release bicarbonate ions, due to the lack of secretin mechanization in the small intestines. The small intestine has a pH in the range of 1.0–1.5 when the bolus of food enters the small intestines. Normally, plasma concentrations of secretin increase when the duodenal pH is below 4.5, and typically doubles during the postprandial period. The s cells in the proximal portion of the small intestines release secretin in response to this low pH. The secretin is then released into the bloodstream and ultimately reaches the pancreas. In response, the pancreas releases bicarbonate ions, water and electrolytes into the small intestines thus neutralizing the pH by bringing it from a 1.0–1.5 to approximately 6.5.

Following this, the pancreas secretes the enzyme trypsin in an inactive form trypsinogen. The trypsinogen is converted to trypsin in the small intestines. In an environment where the pH is 6.5 or greater, the trypsin catalyzes the formation of chymotrypsinogen to chymotrypsin. These enzymes are essential for the digestion of protein. In the absence of protein-digestion, the amino acids necessary for the growth and development of individuals are absent. Therefore, based on tests performed by the present inventor, it is postulated that the increase of protein digestion of an individual suffering from PDD can lead to the improvement of such disorders. Accordingly, since secretin is responsible for aiding in the protein digestion process, it has been determined that the presence of abnormal protein digestion in individuals, especially children, is indicative of which individuals are likely to benefit from the administration of secretin.

Indeed, in accordance with the present invention, experimental results have shown that the potential benefit of administering secretin, other neuropeptides, peptides and/or digestive enzymes to individuals diagnosed with developmental disorders falling within the entire spectrum of PDD may be predetermined by analyzing the measured fecal chymotrypsin levels of such individuals. More specifically, as illustrated below, it has been determined that sub-normal to abnormal levels of fecal chymotrypsin in children/adults with PDD symptoms will benefit from the administration of secretin, other neuropeptides, peptides and/or digestive enzymes. In addition, experimental tests by the present inventor have revealed that the administration of secretin, other neuropeptides, peptides and/or digestive enzymes to others beyond those of who are autistic, especially those diagnosed with ADD and ADHD will benefit from the administration of secretin, other neuropeptides, peptides and/or digestive enzymes.

The following experiments describe exemplary diagnosis and treatment procedures in accordance with the invention. It is to be understood that these experiments and corresponding results are set forth by way of illustration only, and nothing therein shall be construed as a limitation on the overall scope of the invention.

I. EXPERIMENT 1

Figure 13:
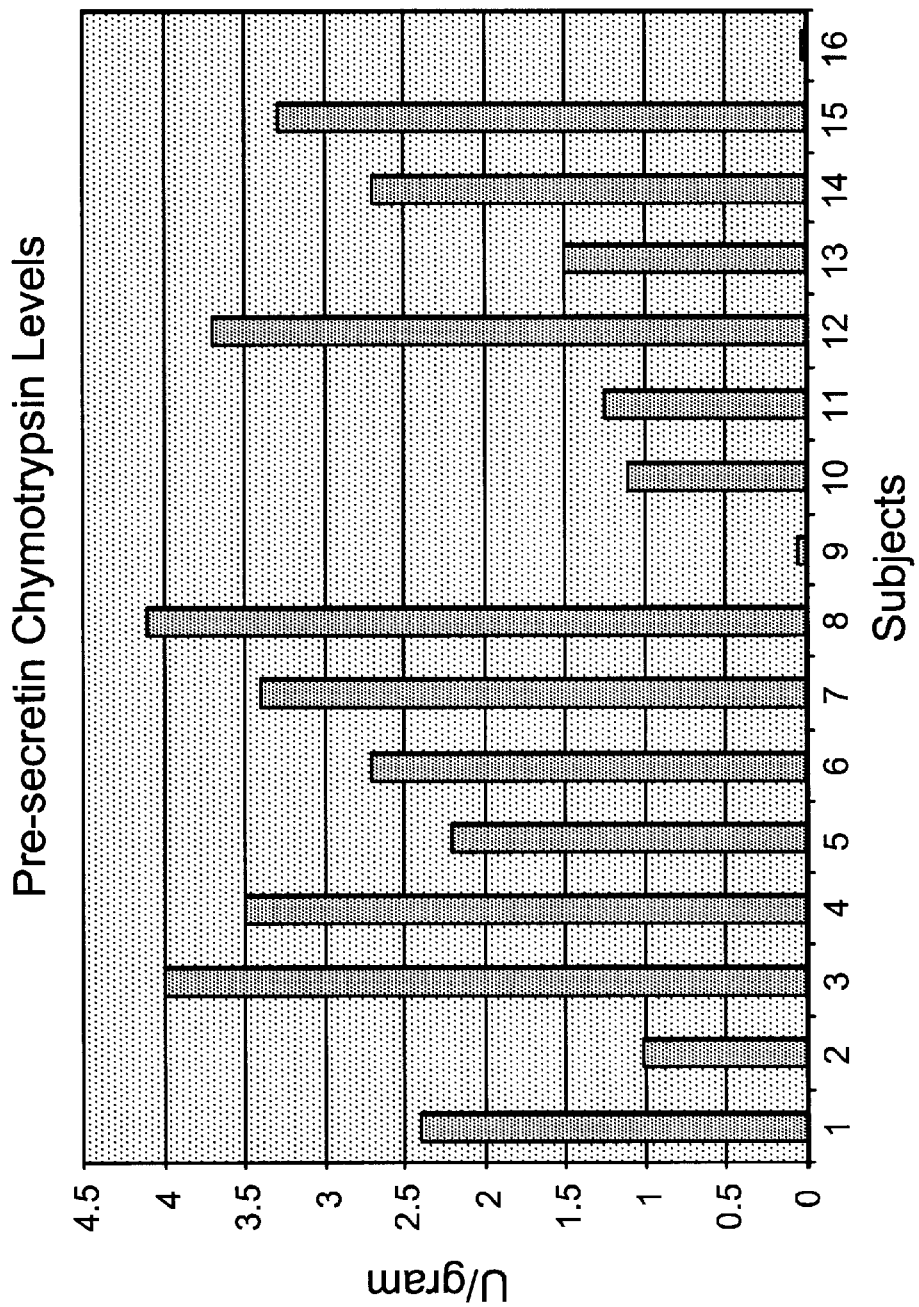
FIG. 13 illustrates the measured fecal chymotrypsin levels of 16 autistic children pre-secretin administration.

In this experiment, 16 children diagnosed as having autism were administered the following Fecal Chymotrypsin Test in accordance with an embodiment of the invention. First, approximately 2 grams of stool were collected from each child and placed in a sterile container (although it is to be understood that any quantity of stool may be collected, as 2 grams of stool is not a required amount). Each stool sample was then analyzed using, e.g., an enzymatic photospectrometry analysis as is known by those skilled in the art, to determine the level of fecal chymotrypsin in the stool. Although the enzymatic photospectrophotometry process is preferred, any suitable conventional method may be used for measuring the fecal chymotrypsin levels. The measured chymotrypsin levels of the 16 autistic children are illustrated in FIG. 13.

After determining the chymotrypsin levels of the stools, each of these levels were compared with threshold chymotrypsin levels to determine if the child was likely to benefit from secretin administration. By way of example, with the fecal chymotrypsin tests of the stool samples being performed at 30° C., normal levels of chymotrypsin are deemed to lie above 8.4 U/gram, whereas pathologically abnormal levels are deemed to lie below 4.2 U/gram. In addition, chymotrypsin levels between 8.4 U/gram and 4.2 U/gram are considered equivocal, and further testing of the individual's fecal chymotrypsin levels over a period of time should be performed. It is to be noted that as shown in FIG. 13, all of the 16 autistic children that were tested had abnormal levels of fecal chymotrypsin pre-secretin administration.

Another stool sample was then collected from each child two days after the first test and analyzed to determine the chymotrypsin levels. This second test is preferably performed to obtain additional chymotrypsin measurements to make a more accurate determination. Those children having abnormal levels of chymotrypsin in their stools are considered candidates for secretin administration. Other factors that may be considered in determining which children are potential candidates for secretin administration aside from the fecal chymotrypsin levels include a previously diagnosed history of autism, a history of gastrointestinal (GI) dysfunction, including any history of protracted diarrhea or constipation lasting for a weeks or months, as well as a self-limiting diet consisting primarily of carbohydrates.

Upon determining that a given child was likely to benefit from secretin administration based on the results of the fecal chymotrypsin test, the child was administered a CARS (Childhood Autism Rating Scale) test prior to being scheduled for secretin infusion.

For each of the 16 autistic children tested, a preferred secretin infusion process according to the present invention was performed involving the administering of 1 U/kg of body weight of Secretin-Ferring for a period of nine months at intervals of approximately 6 weeks. In addition, another CARS test was administered to each of the 16 autistic children 3 weeks post secretin administration to determine if their autism had changed post infusion.

A preferred secretin infusion process includes the initial step of prepping an arm of the candidate child with an IV injection of saline. A test dose of 1 U of Secretin-Ferring is then administered to the child. Approximately one minute after infusion, the child is examined for signs of allergic reaction including rash, increased heart rate, and increase of blood pressure. If the child does not display any signs of allergic reaction, the remaining units of Secretin-Ferring is administered to the child in the manner of an IV push, which is then followed by a saline flush. Subsequently, each child receives a 1 U/kg of body weight infusion of Secretin-Ferring approximately every 6 weeks for 9 months. It is to be understood that any commercially available form of secretin may be used.

Results of Experiment 1

Figure 14:
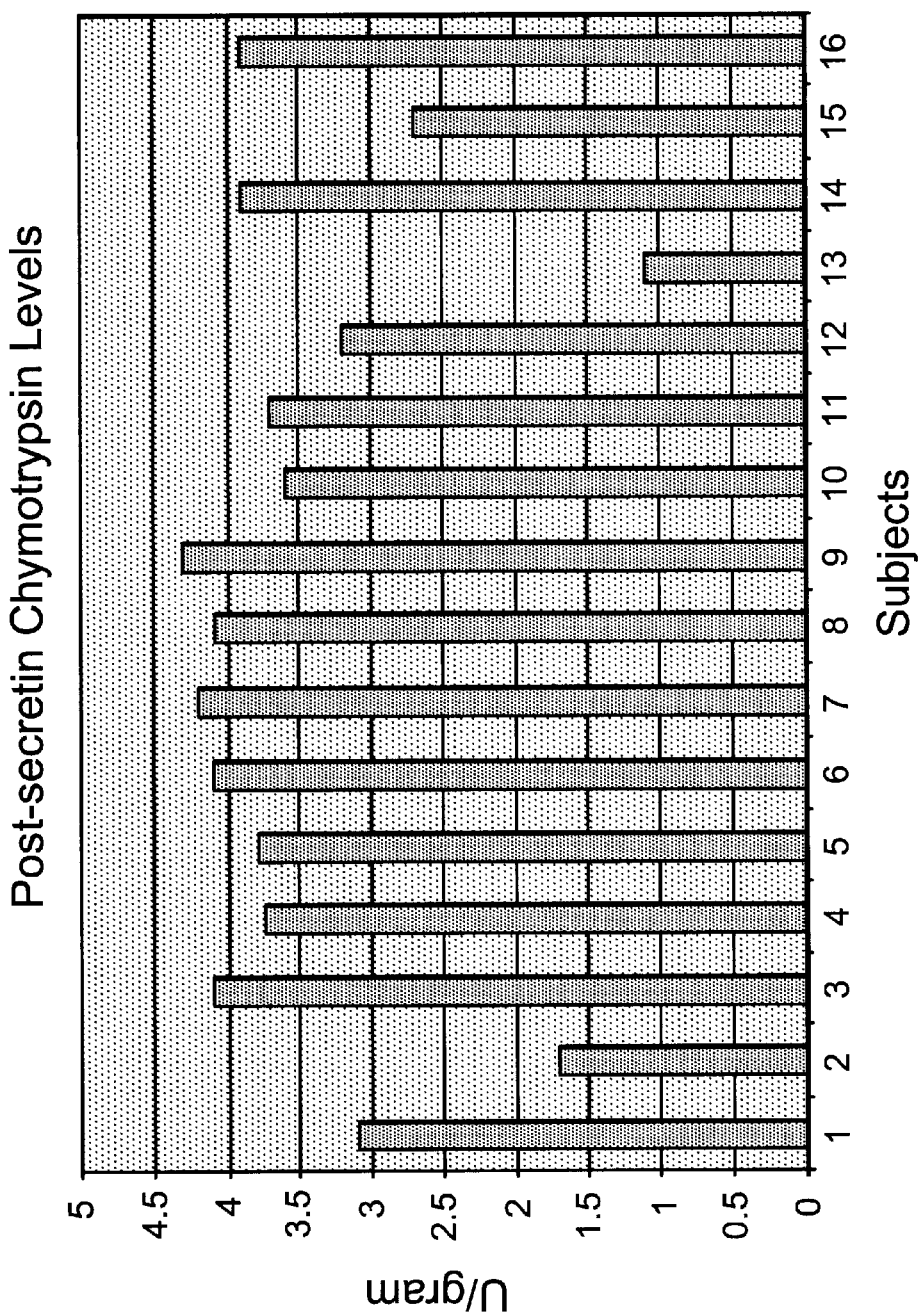
FIG. 14 illustrates the measured fecal chymotrypsin levels of the 16 autistic children approximately one week post-secretin administration.

The results of Experiment 1 are illustrated in FIGS. 1–14. For instance, approximately one week after the first secretin infusion, the fecal chymotrypsin level of each of the 16 autistic children was measured again. The results of this test are illustrated in FIG. 14. As shown, the chymotrypsin level of each of the 16 autistic children test increased post-secretin administration (as compared with the levels shown in FIG. 13).

Figure 2:
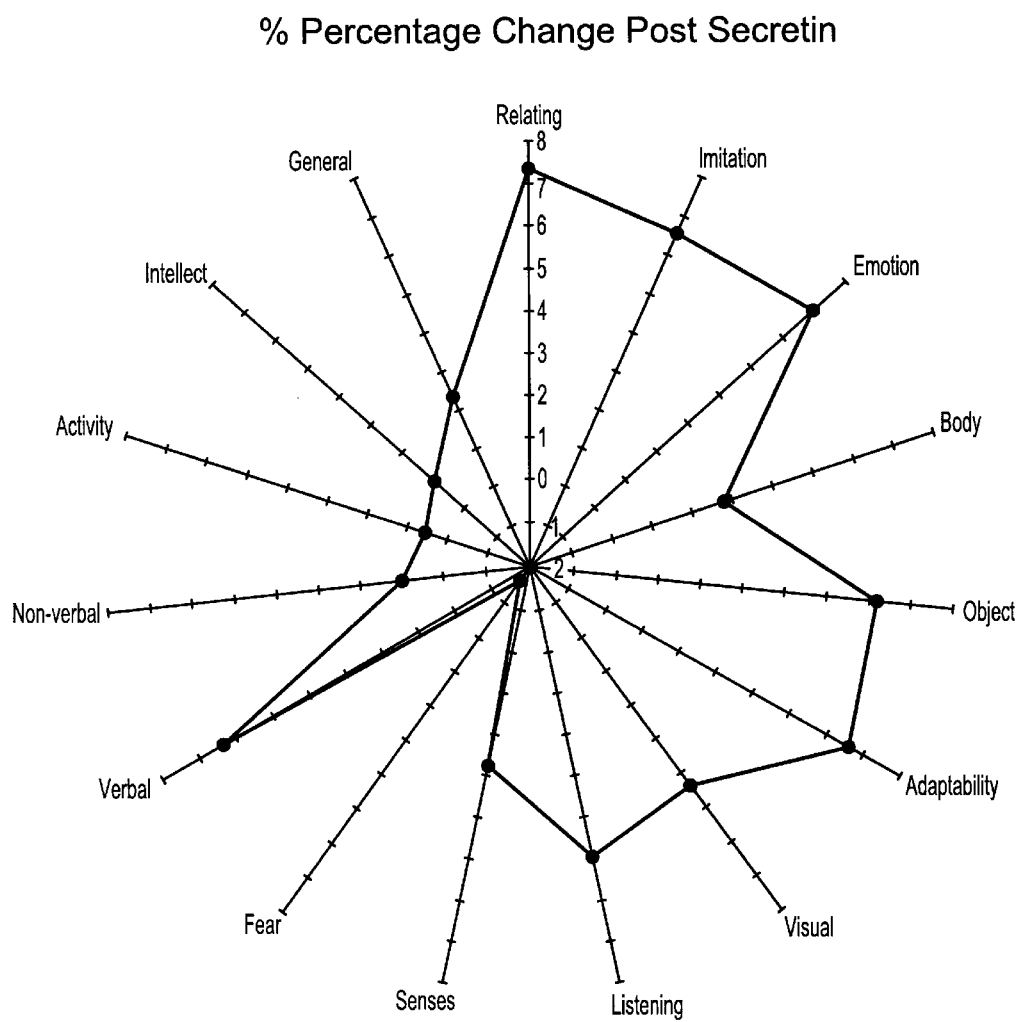
FIG. 2 illustrates percentage change from pre-secretin to post-secretin administration in the average scores of the respective components of the CARS test of FIG. 1.
Figure 3:
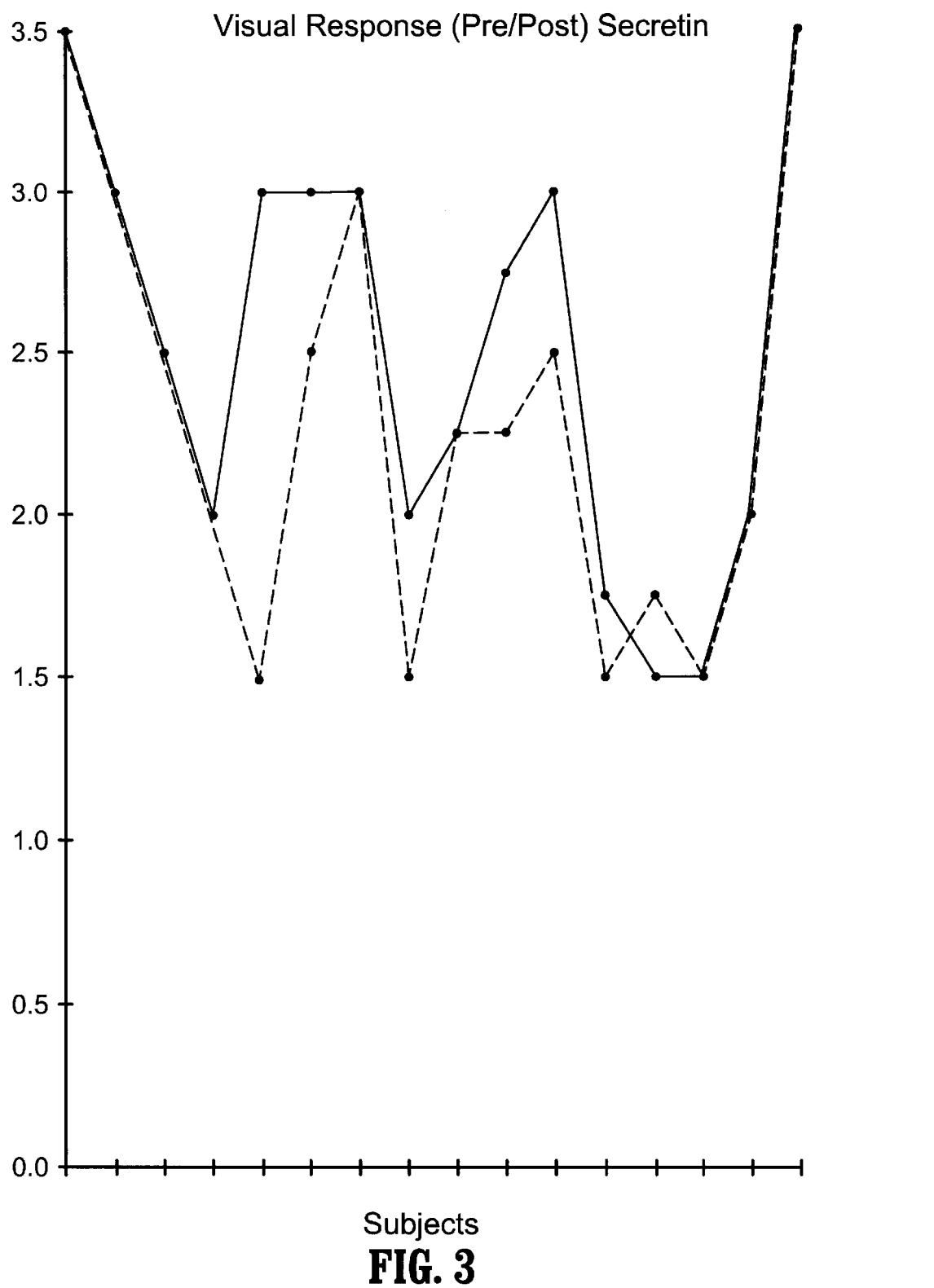
FIG. 3 illustrates the change in CARS scores for the sub-class Visual response from pre-secretin administration to three weeks post-secretin administration, where the solid lines indicate pre-secretin scores and the dotted lines indicate post-secretin scores.
Figure 4:
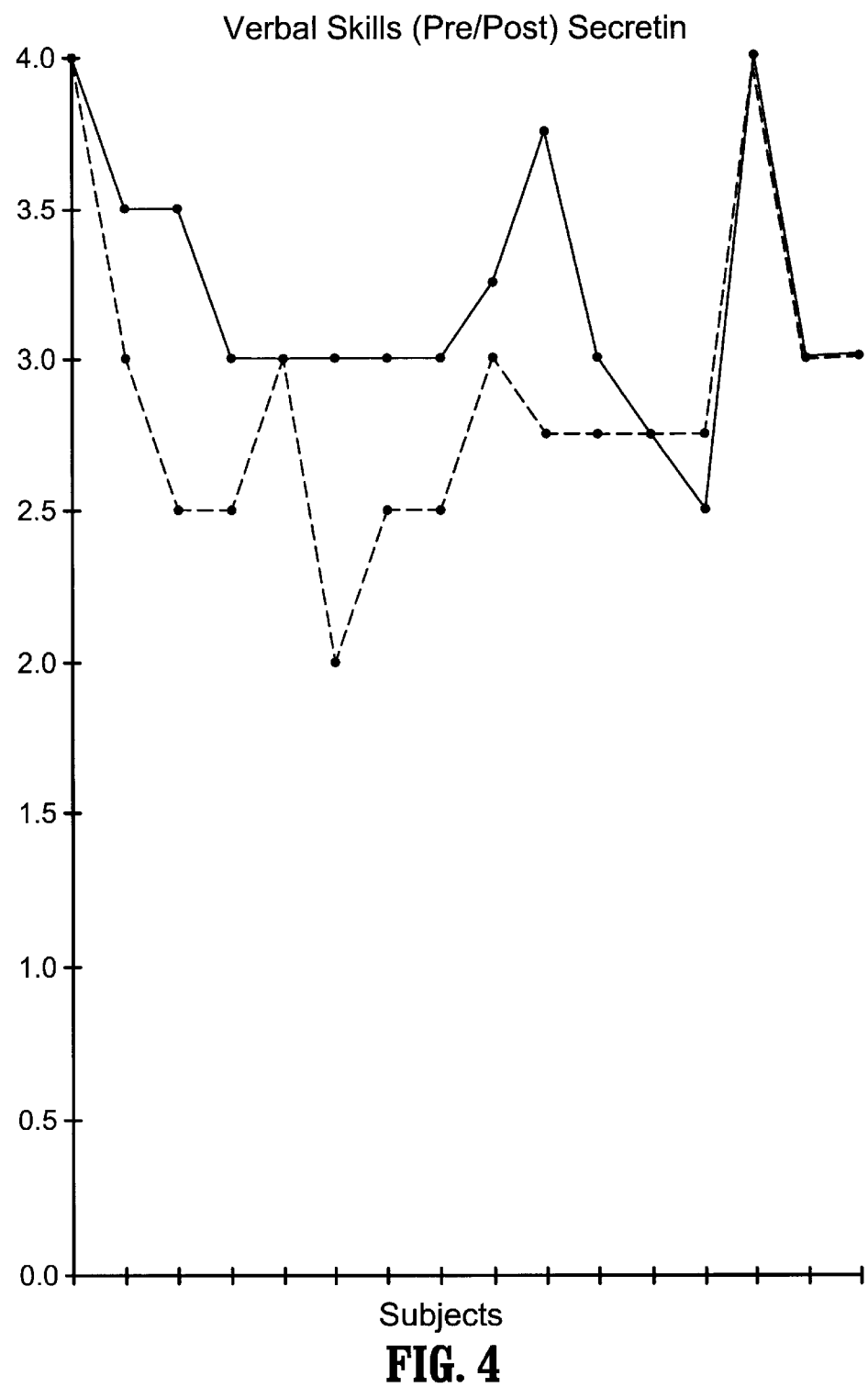
FIG. 4 illustrates the change in CARS scores for the sub-class Verbal Skills from pre-secretin administration to three weeks post-secretin administration, where the solid lines indicate pre-secretin scores and the dotted lines indicate post-secretin scores.
Figure 5:
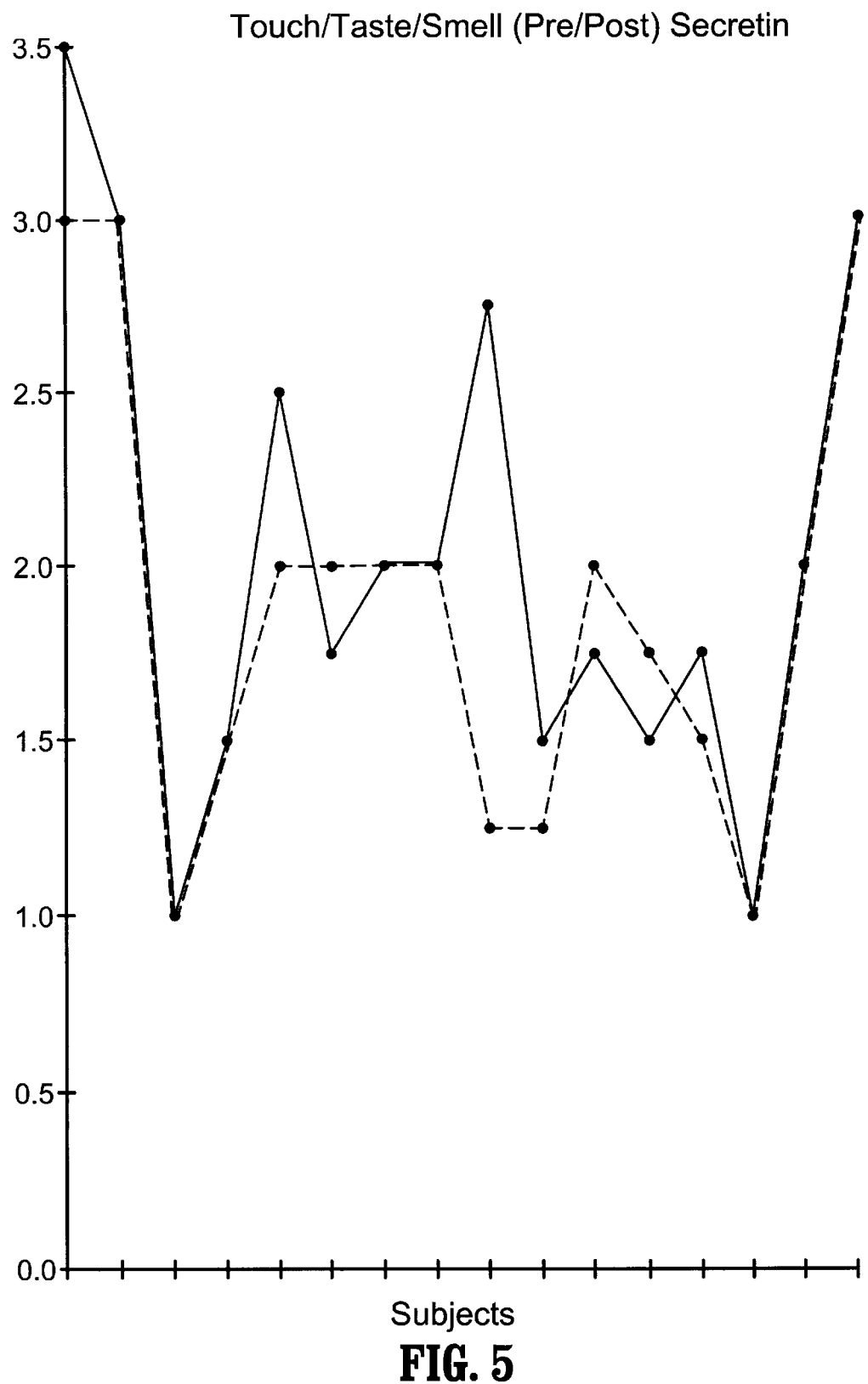
FIG. 5 illustrates the change in CARS scores for the sub-class Touch/Taste/Smell from pre-secretin administration to three weeks post-secretin administration, where the solid lines indicate pre-secretin scores and the dotted lines indicate post-secretin scores.
Figure 6:
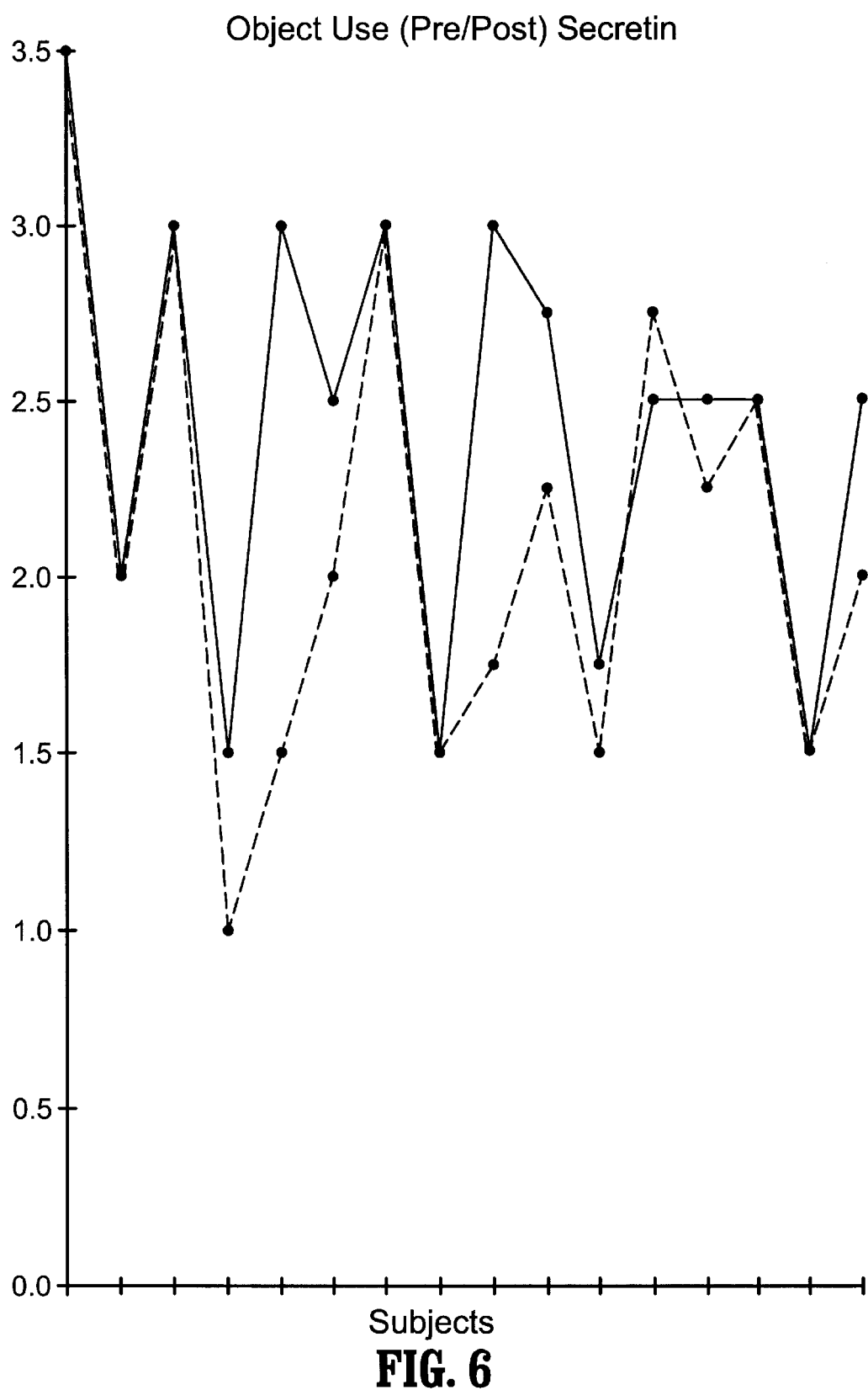
FIG. 6 illustrates the change in CARS scores for the sub-class Object Use from pre-secretin administration to three weeks post-secretin administration, where the solid lines indicate pre-secretin scores and the dotted lines indicate post-secretin scores.
Figure 7:
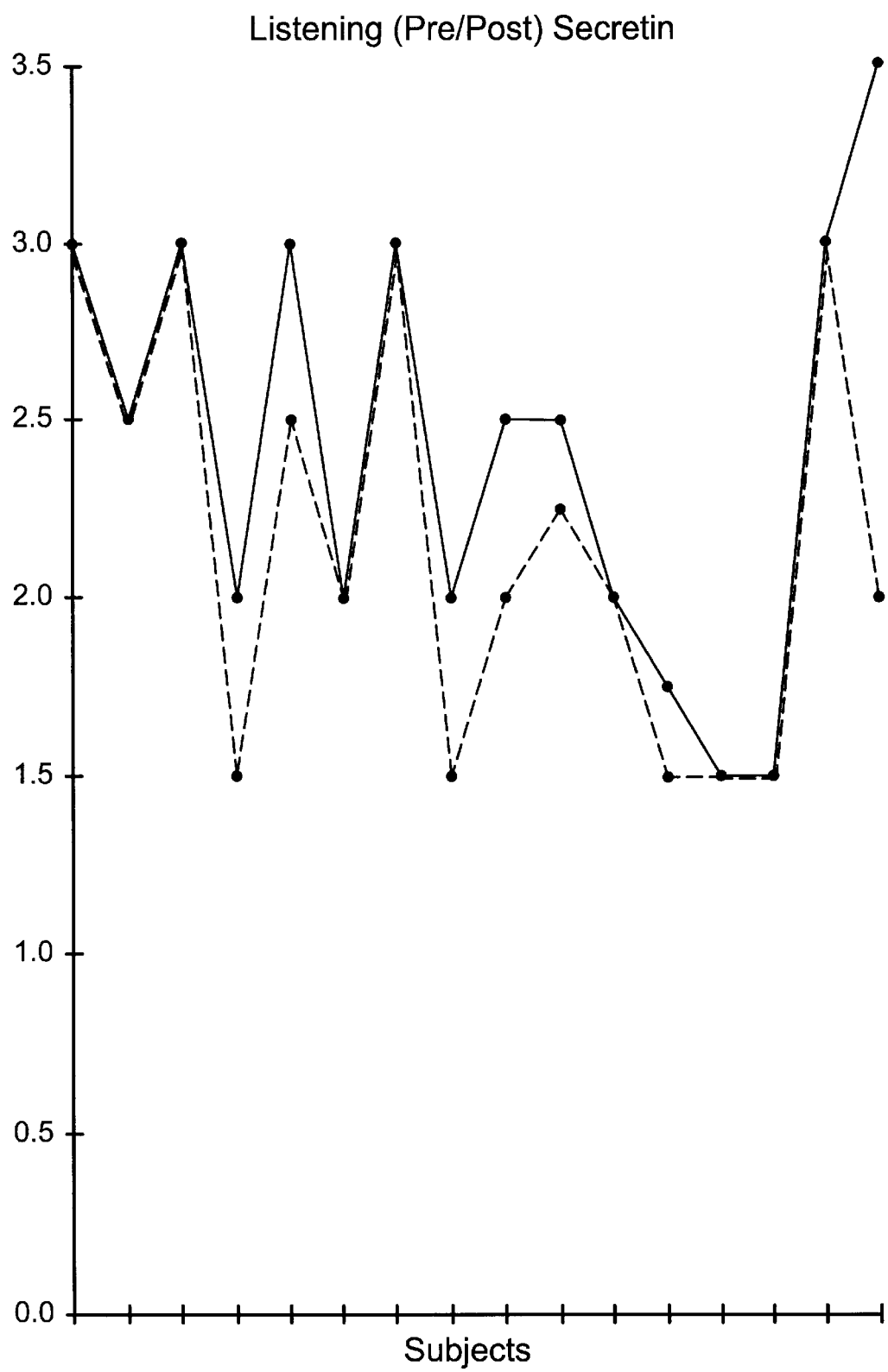
FIG. 7 illustrates the change in CARS scores for the sub-class Listening from pre-secretin administration to three weeks post-secretin administration, where the solid lines indicate pre-secretin scores and the dotted lines indicate post-secretin scores.
Figure 8:
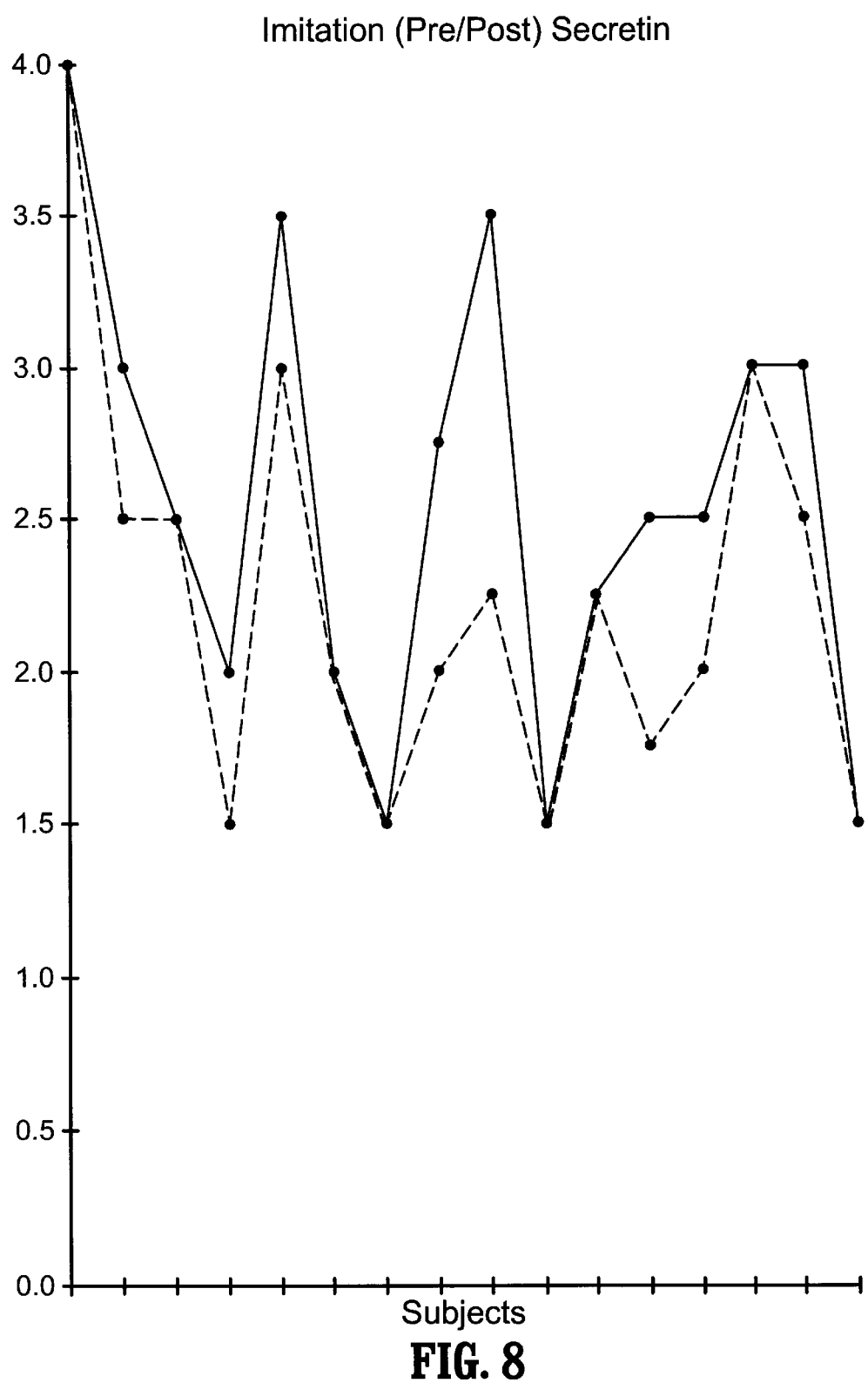
FIG. 8 illustrates the change in CARS scores for the sub-class Imitation from pre-secretin administration to three weeks post-secretin administration, where the solid lines indicate pre-secretin scores and the dotted lines indicate post-secretin scores.
Figure 9:
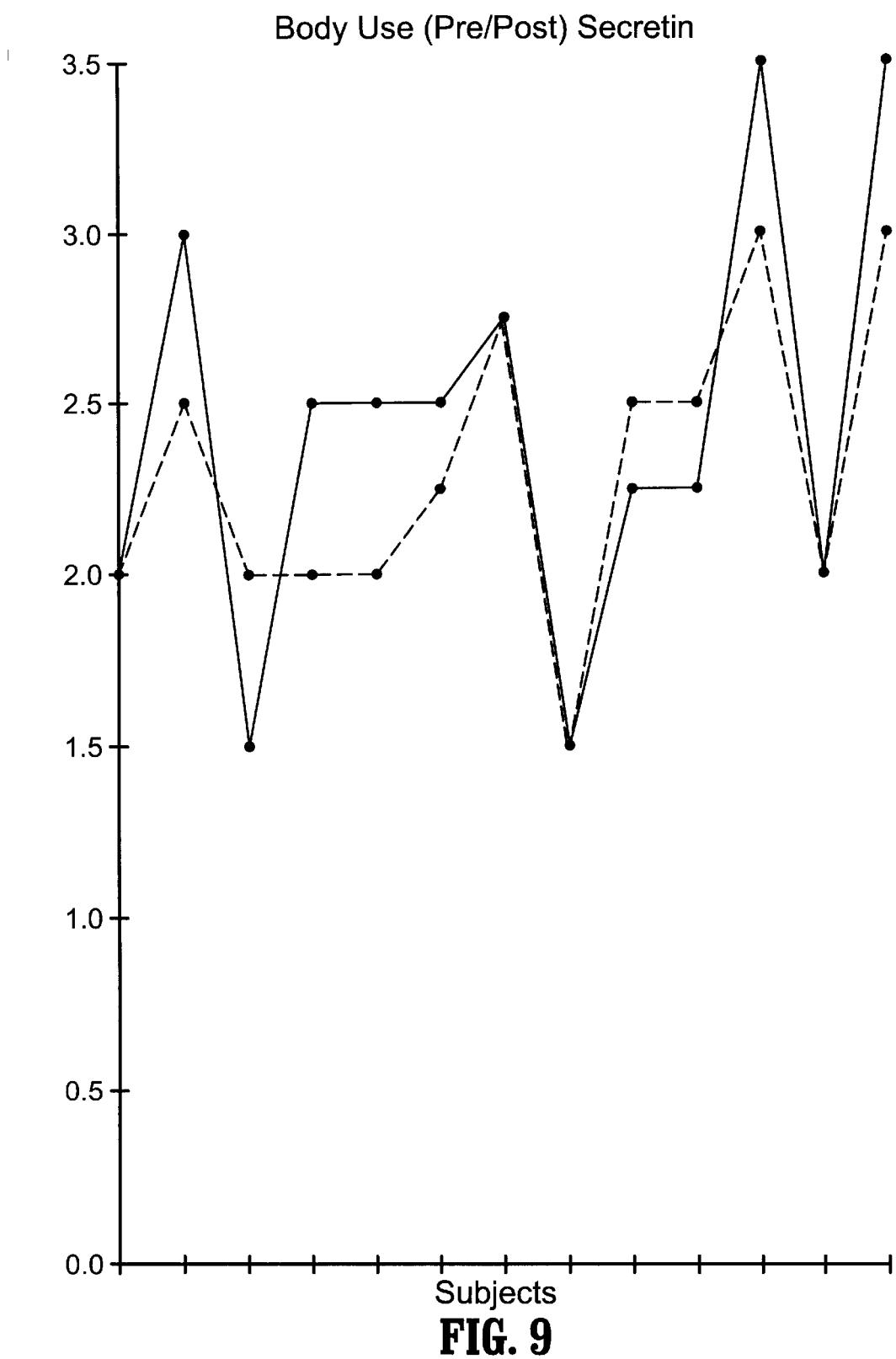
FIG. 9 illustrates the change in CARS scores for the sub-class Body Use from pre-secretin administration to three weeks post-secretin administration, where the solid lines indicate pre-secretin scores and the dotted lines indicate post-secretin scores.
Figure 10:
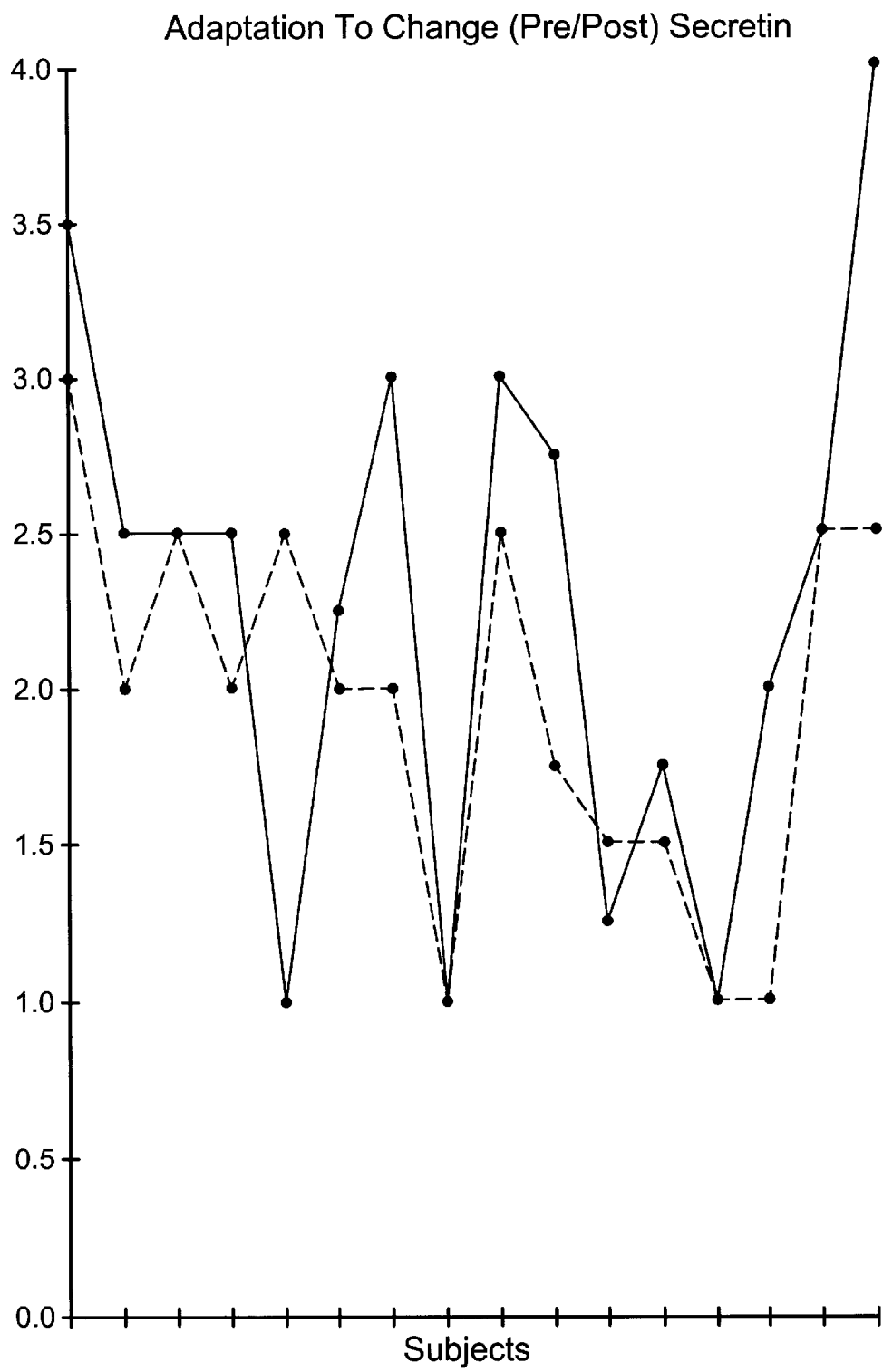
FIG. 10 illustrates the change in CARS scores for the sub-class Adaptation to Change from pre-secretin administration to three weeks post-secretin administration, where the solid lines indicate pre-secretin scores and the dotted lines indicate post-secretin scores.
Figure 11:
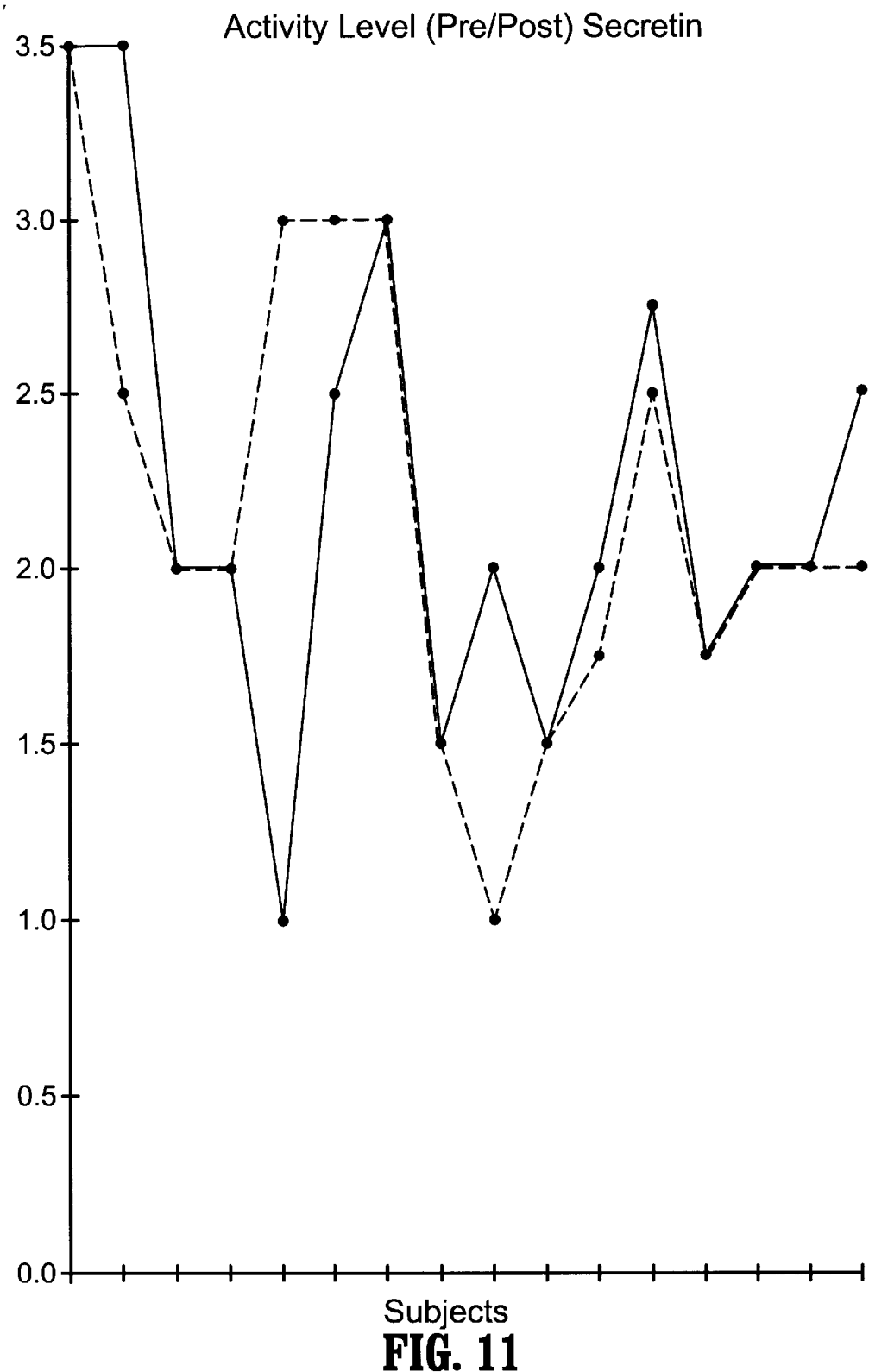
FIG. 11 illustrates the change in CARS scores for the sub-class Activity Level from pre-secretin administration to three weeks post-secretin administration, where the solid lines indicate pre-secretin scores and the dotted lines indicate post-secretin scores.
Figure 12:
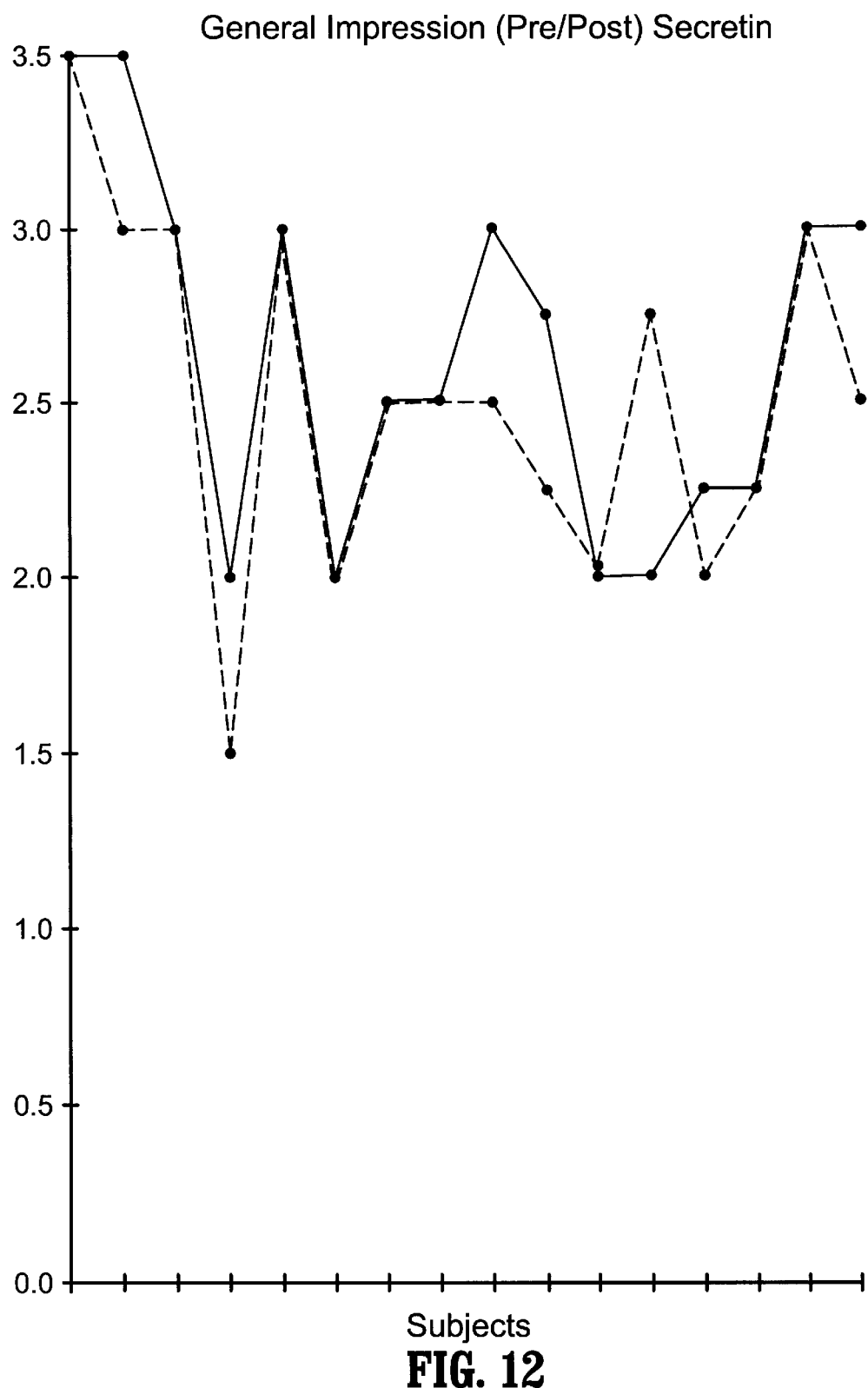
FIG. 12 illustrates the change in CARS scores for the sub-class General Impression from pre-secretin administration to three weeks post-secretin administration, where the solid lines indicate pre-secretin scores and the dotted lines indicate post-secretin scores.

In addition, FIG. 1 illustrates the pre-secretin CARS test results (solid line) and the post-secretin CARS test results (dotted line) for each of the 16 autistic children tested approximately 3 weeks after the first secretin administration. Most notably, FIG. 1 illustrates an overall decrease in the CARS scores indicating improvements in the PDD/autistic symptoms of the children. In particular, FIG. 2 illustrates respective percentage decreases in components of CARS scores, wherein the numbers represent percentage change in the average of the scores in each component of the CARS test post-secretin administration. In particular, FIGS. 3–12 illustrate the improved scores of each of the 16 autistic children for the individual components of the CARS scores. As shown, the component scores demonstrated improvement except for the fear component which increased 3 weeks post infusion.

II. EXPERIMENT 2

In this experiment, 37 autistic children with abnormal fecal chymotrypsin levels were administered secretin over the course of 6 months using the secretin infusion process described above. Their fecal chymotrypsin (FC) levels were measured weekly using the fecal chymotrypsin test described above.

Results of Experiment 2

Out of the 37 autistic children tested, the fecal chymotrypsin levels of 34 children had returned to normal after 6 months, the fecal chymotrypsin levels of 2 children moved to equivocal, and the fecal chymotrypsin level of 1 child remained abnormal. These results of this experiment are listed in the following Table 1.

TABLE 1

| Autistic Children Tested | Pre-Secretin Administration | 6 Months Post-Secretin Administration |
| --- | --- | --- |
| # Autistic Children w/Abnormal FC levels | 37 | 1 |
| # Autistic Children w/Equivocal FC levels | 0 | 2 |
| # Autistic Children w/normal FC levels | 0 | 34 |

III. EXPERIMENT 3

Figure 15:
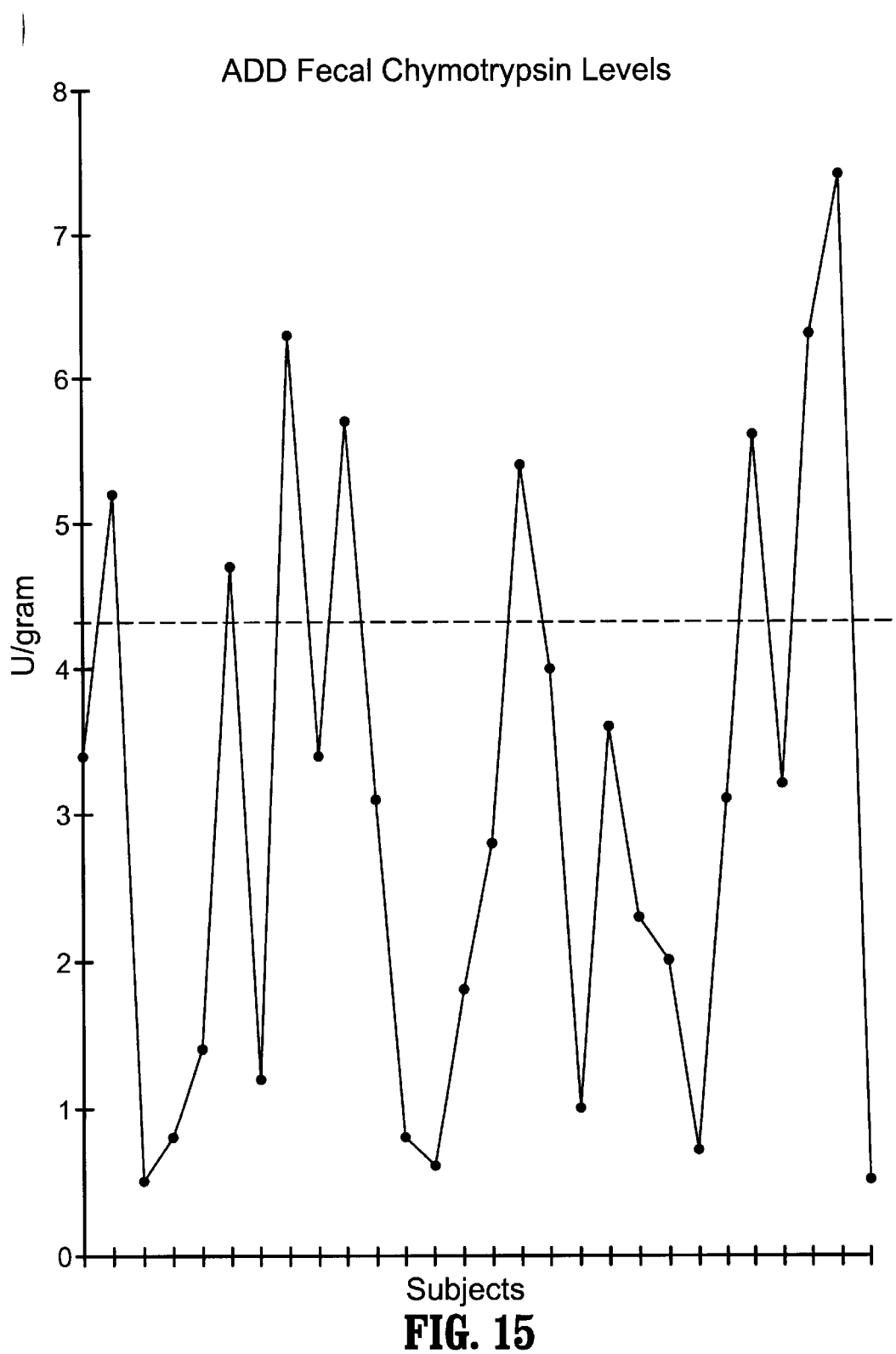
FIG. 15 illustrates the measured fecal chymotrypsin levels of 28 ADD children.

In this experiment, the fecal chymotrypsin levels of 28 children diagnosed with ADD were obtained using the fecal chymotrypsin test described above in Experiment 1. FIG. 15 illustrates the measured fecal chymotrypsin levels of these 28 children. It is to be noted that, as shown in FIG. 15, all of the 28 ADD children were found to have sub-normal fecal chymotrypsin levels since all of the values fell below 8.4 U/g. More specifically, 8 out of 28 children were determined to have an equivocal fecal chymotrypsin level and 20 out of the 28 children were determined to have a pathologic level of fecal chymotrypsin. As noted above, a chymotrypsin level of 8.4 U/g is considered a reference value for normal levels of chymotrypsin.

Of these 28 children who were diagnosed with ADD and abnormal fecal chymotrypsin levels, 10 were administered digestive enzymes comprising amylase, proteases, lipases, sucrase, maltase, and other digestive enzymes. These digestive enzymes were administered one tablet at each mealtime (i.e., three times a day), adjusted for the age and weight of the child. More specifically, for the ADD children ages 1–6, a quantity of digestive enzymes of approximately 4,000–8,000 U.S.P. Units/tablet comprising lipase, amylase and protease were administered. For the ADD children of ages 7–12, a quantity of digestive enzymes of approximately 8,000–12,000 U.S.P. Units/tablet comprising lipase, amylase and protease were administered. Other digestive enzymes that were administered in smaller quantities included cellulase, sucrase and maltase. These digestive enzymes were administered over a period of 6 months.

Results of Experiment 3

At the time of this experiment, 4 out of the 10 children who were administered the digestive enzymes were taking Ritalin. As is known in the art, Ritalin is a stimulant medication used to treat children and adults with ADD and ADHD. More specifically, it is used to treat hyperactivity and attention problems. As a result of the administration of the digestive enzymes, all of the 4 children who had been taking Ritalin were able to completely stop taking the Ritalin. In addition, significant improvements in the behavior of the other 6 children were noted. These results are shown in the following Table 2:

TABLE 2

| | |
| --- | --- |
| # ADD Children w/Sub-normal FC levels | 28 |
| # of the 28 ADD Children With Abnormal FC levels That Were Administered Digestive Enzymes | 10 |
| # of the 10 ADD Children That Were Administered Digestive Enzymes Who Were Taking Ritalin | 4 |
| # ADD Children Requiring Ritalin Administration 6 months Post Administration of Digestive Enzymes | 0 |

IV. EXPERIMENT 4

Figure 16:
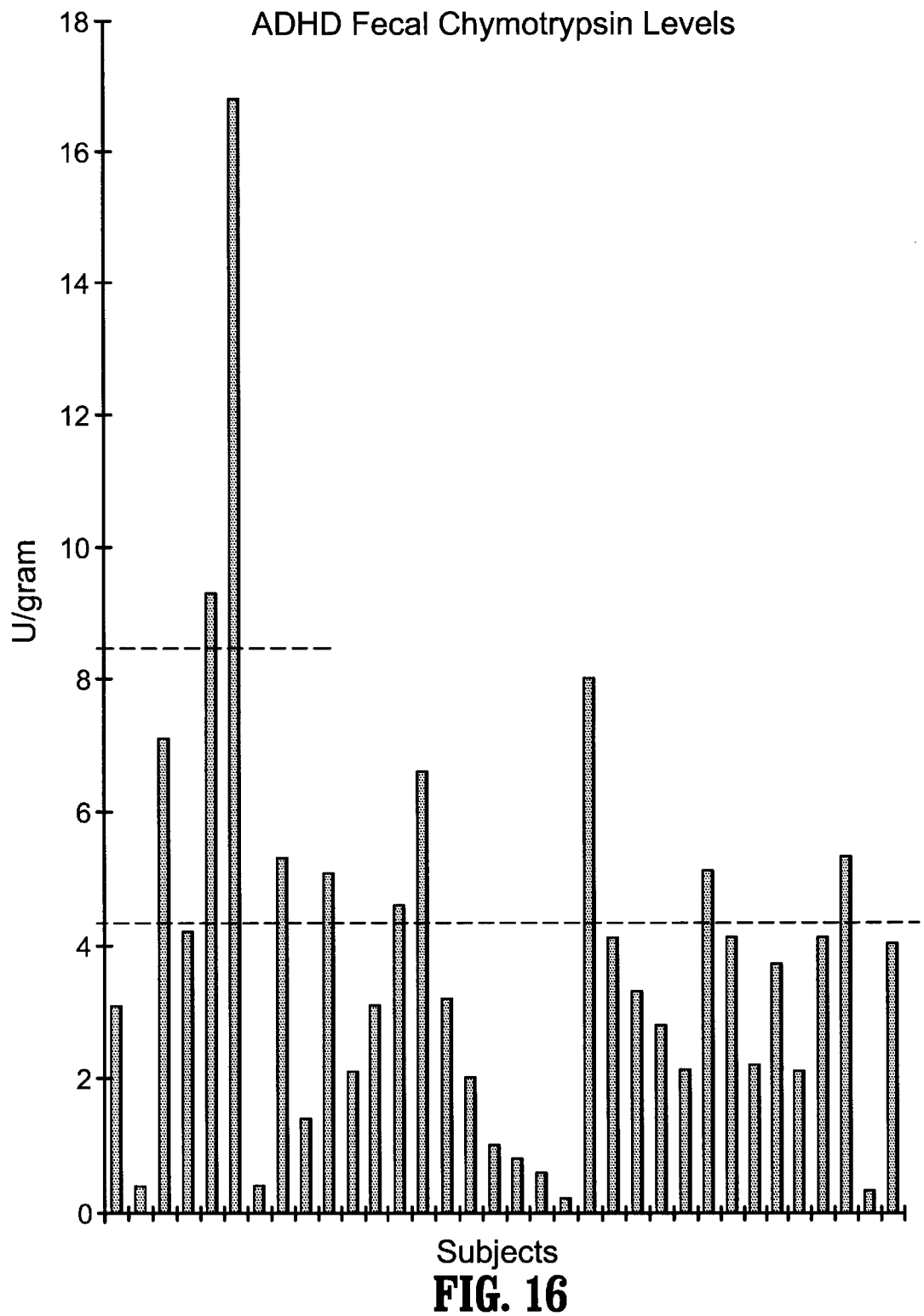
FIG. 16 illustrates the measured fecal chymotrypsin levels of 34 ADHD children.

In this experiment, the fecal chymotrypsin levels of 34 children diagnosed with ADHD were obtained using the fecal chymotrypsin test described above in Experiment 1, the levels of which are illustrated in FIG. 16. As shown, 32 children out of 34 children tested were determined to have sub-normal fecal chymotrypsin levels. It is to be further noted that 24 of the 34 children were found to have pathologic levels of fecal chymotrypsin.

To determine the effect of secretin administration on ADHD children, 5 of the 24 children having a pathologic fecal chymotrypsin level were administered secretin using the secretin infusion process described above.

Results of Experiment 4

Figure 17:
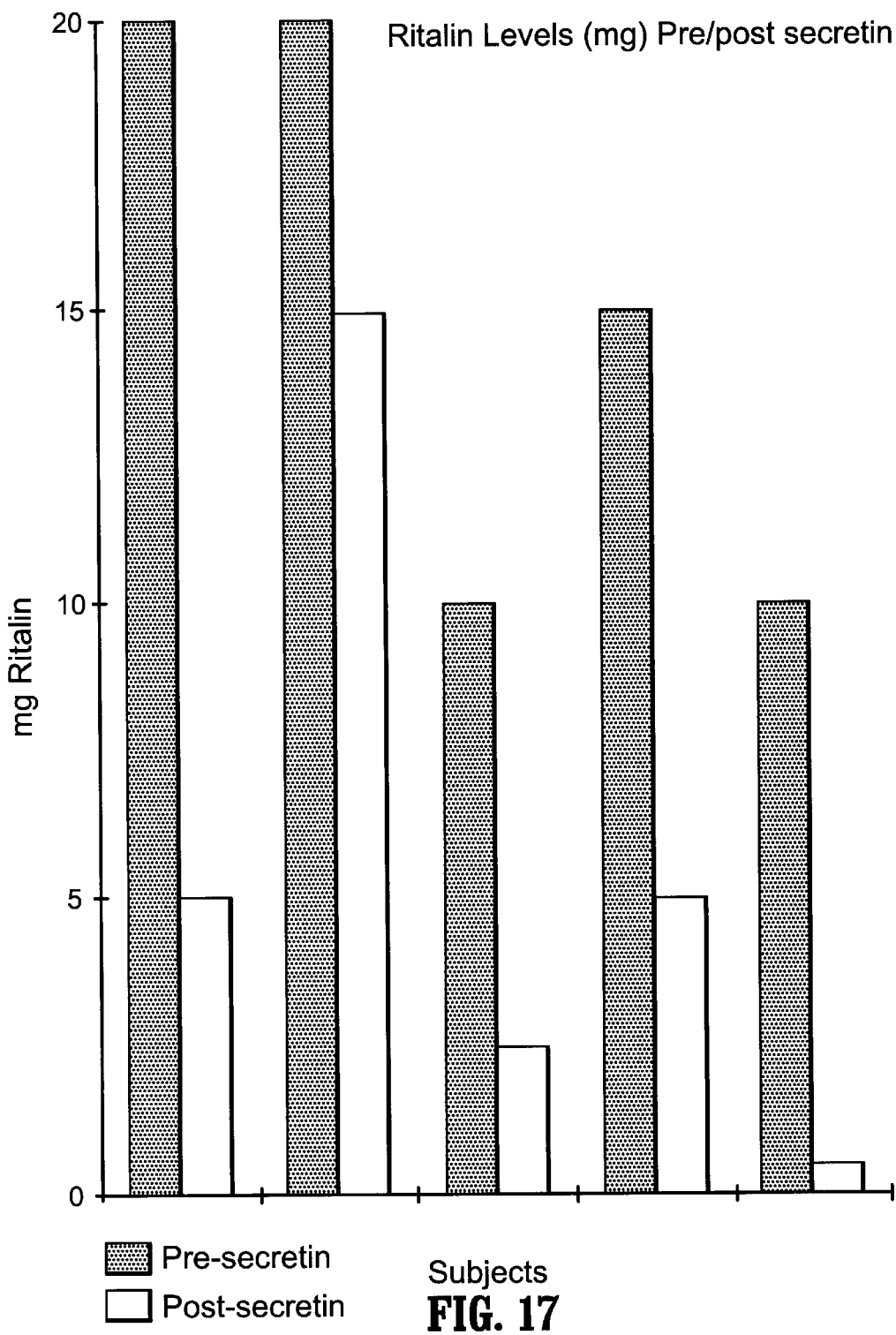
FIG. 17 illustrates Ritalin levels administered before and after secretin administration in five of the ADHD children in FIG. 16, where the shaded bars indication pre-secretin Ritalin levels and the non-shaded bars indicate post-secretin Ritalin levels.

The results of this experiment are set forth in FIG. 17, which illustrates the required levels of Ritalin (in mg) of the 5 children tested both pre-secretin administration (as indicated by the shaded bars) and 6 months post-secretin administration (as indicated by the non-shaded bars). It is to be appreciated that as shown in FIG. 17, each of the 5 children who were administered secretin demonstrated significant changes post-secretin administration with respect to the level of Ritalin (mg) that each child needed to remain at the same functional level as their functional level prior to secretin administration.

V. EXPERIMENT 5

In this experiment, to determine the effect of the administration of digestive enzymes to ADHD children, 9 children of the 34 children diagnosed with ADHD (in experiment 4 described above) whose fecal chymotrypsin levels were determined to be pathologic were administered digestive enzymes. Such digestive enzymes included amylase, lipase, proteases, sucrases, maltase, and other digestive enzymes. Each child was administered 1 tablet of digestive enzymes at each mealtime (i.e., three times a day), adjusted for age and weight of the child. More specifically, for the ADHD children ages 1–6, a quantity of digestive enzymes of approximately 4,000–8,000 U.S.P. Units/tablet comprising lipase, amylase and protease were administered. For the ADHD children of ages 7–12, a quantity of digestive enzymes of approximately 8,000–12,000 U.S.P. Units/tablet comprising lipase, amylase and protease were administered. Other digestive enzymes that were administered in smaller quantities included cellulase, sucrase and maltase. The digestive enzymes were administered over a 6 month period.

Results of Experiment 5

It is to be appreciated that as a result of the administration of digestive enzymes over the 6 month period, all 9 children were able to reduce their required Ritalin levels. Most notably, 2 of the 9 children were able to stop taking Ritalin after 6 months of digestive enzyme administration. The results of experiment 5 are illustrated in the following Table 3:

TABLE 3

| | |
|---|---|
| # ADHD Children w/Abnormal FC levels Who Were Administered Digestive Enzymes | 9 |
| # Of The 9 ADHD Children Whose Ritalin Levels Were Reduced 6 months Post-Digestive Enzyme Administration | 9 |
| # Of The 9 ADHD Children Who Stopped Taking Ritalin 6 Months Post-Digestive Enzyme Administration | 2 |

In summary, the results of the experiments described herein demonstrate that the potential benefit of the administration of secretin, other neuropeptides, peptides and/or digestive enzymes to an individual diagnosed with developmental disorders falling within the entire spectrum of PDD may be determined by analyzing the measured fecal chymotrypsin level of the individual. Indeed, as illustrated above, a child suffering from a disorder such as autism, ADD and ADHD, for example, and having sub-normal to abnormal levels of fecal chymotrypsin will benefit from the administration of secretin, other neuropeptides, peptides and/or digestive enzymes. In addition, the experimental results have indicated that the administration of secretin, other neuropeptides, peptides and/or digestive enzymes to such individuals results in significant amelioration of the symptomatologies of such disorders.

Although illustrative embodiments have been described herein with reference to the accompanying drawings, it is to be understood that the present invention is not limited to those precise embodiments, and that various other changes and modifications may be affected therein by one skilled in the art without departing from the scope or spirit of the invention. All such changes and modifications are intended to be included within the scope of the invention as defined by the appended claims.

What is claimed is:

1. A therapeutic method for treating an individual diagnosed with a pervasive development disorder (PDD), comprising the steps of:

comparing a fecal chymotrypsin level of the individual with a normal fecal chymotrypsin level; and administering secretin therapy to the individual if the fecal chymotrypsin level of the individual is below the normal fecal chymotrypsin level.

2. The method of claim 1, wherein the normal fecal chymotrypsin level is about 8.4 U/gm.

3. The method of claim 1, wherein the normal fecal chymotrypsin level is about 4.2 U/gm.

4. The method of claim 1, comprising the step of determining the individual's fecal chymotrypsin level by an enzymatic photospectrophotometry analysis.

5. The method of claim 1, wherein the step of administering secretin therapy to the individual comprises administering a therapeutic dose of secretin to the individual at approximately 6 week time intervals.

6. The method of claim 5, wherein therapeutic dose is at least 1 U/kg of body weight.

7. The method of claim 6, further comprising the steps of testing the individual pre-secretin administration and post secretin administration to determine if the PDD has improved.

8. The method of claim 1, wherein the PDD is one of autism, ADD (attention deficit disorder), or ADHD (attention deficit hyperactivity disorder).

* * * * *